US012776392B2

(12) United States Patent
Park et al.

(10) Patent No.: US 12,776,392 B2
(45) Date of Patent: Oct. 27, 2026

(54) ENABLING MULTI-MODAL SEMANTIC SEARCH FOR COMPLEX MATERIALS TO FACILITATE MATERIALS DESIGN AND DEVELOPMENT TASKS BY FOUNDATION MODELS

(71) Applicant: International Business Machines Corporation, Armonk, NY (US)

(72) Inventors: Nathaniel H. Park, San Jose, CA (US); Tim Erdmann, San Jose, CA (US); James L. Hedrick, Pleasanton, CA (US); Sarathkrishna Swaminathan, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 18/798,970

(22) Filed: Aug. 9, 2024

(65) Prior Publication Data

US 2026/0045327 A1 Feb. 12, 2026

(51) Int. Cl.
*G16C 20/90* (2019.01)
*G16C 20/80* (2019.01)

(52) U.S. Cl.
CPC ............. *G16C 20/90* (2019.02); *G16C 20/80* (2019.02)

(58) Field of Classification Search
CPC ........ G16C 20/90; G16C 20/80; G16C 20/20; G16C 20/70; G16C 20/40; G16B 5/00; G16B 40/20
USPC .......... 707/693, 741, 758, 999.003, 999.104, 707/E17.002, E17.014, 687, 736, 760, 707/941, 999.001
See application file for complete search history.

(56) References Cited

U.S. PATENT DOCUMENTS

| | | | | |
|---|---|---|---|---|
| 10,572,545 | B2 | 2/2020 | Oh et al. | |
| 10,896,744 | B2 | 1/2021 | Maxson et al. | |
| 11,087,861 | B2 | 8/2021 | Takeda et al. | |
| 11,100,413 | B2 | 8/2021 | Spangler et al. | |
| 2006/0241926 | A1* | 10/2006 | Nottebaum ............ | G16C 20/20 703/11 |
| 2015/0051889 | A1 | 2/2015 | Ohrn et al. | |
| 2021/0174910 | A1* | 6/2021 | Kwon .................... | G06N 3/045 |
| 2021/0210317 | A1* | 7/2021 | Mistrik .................. | G16C 20/40 |
| 2022/0293216 | A1 | 9/2022 | Park et al. | |

(Continued)

FOREIGN PATENT DOCUMENTS

| | | | |
|---|---|---|---|
| CN | 117690514 | A | 3/2024 |
| JP | 4895689 | B2 | 3/2012 |

OTHER PUBLICATIONS

Rebello et al., BigSMARTS: A Topologically Aware Query Language and Substructure Search Algorithm for Polymer Chemical Structures, J. Chem. Inf. Model. 2023, 63, 6555-6568.

(Continued)

*Primary Examiner* — Md I Uddin
(74) *Attorney, Agent, or Firm* — Kelsey M. Skodje, Esq.; Rachel L. Pearlman, Esq.; Heslin Rothenberg Farley & Mesiti

(57) ABSTRACT

A method for receiving a domain specific language description of a chemical structure; converting the domain specific language description of the chemical structure into a first graphical representation of the chemical structure; encoding the first graphical representation of the chemical structure into a first vector; and storing the first vector into a searchable database.

16 Claims, 5 Drawing Sheets

(56) References Cited

U.S. PATENT DOCUMENTS

| | | | | |
|---|---|---|---|---|
| 2023/0035690 | A1* | 2/2023 | Robey | G16B 5/00 |
| 2023/0052677 | A1* | 2/2023 | Eser | G06N 3/045 |
| 2025/0239333 | A1* | 7/2025 | Brady | G16C 20/40 |

OTHER PUBLICATIONS

Park et al., Artificial intelligence driven design of catalysts and materials for ring opening polymerization using a domain-specific language, Nature Communications, 2023, 14:3686.

Coley et al., A graph-convolutional neural network model for the prediction of chemical reactivity, Chem. Sci., 2019, 10, 370-377.

Vaskin et al., Optimizing substructure search: a novel approach for efficient querying in large chemical databases, arXiv:2310.02022v1 [cs.DB] Oct. 3, 2023.

* cited by examiner

ENABLING MULTI-MODAL SEMANTIC SEARCH FOR COMPLEX MATERIALS TO FACILITATE MATERIALS DESIGN AND DEVELOPMENT TASKS BY FOUNDATION MODELS

BACKGROUND

The present disclosure relates to chemical structures, and more specifically, to databases storing information about chemical structures. A chemical database system refers to a system designed to store, manage, and retrieve, among other things, information about chemical compounds and their properties. These systems can facilitate data sharing, computational analysis, and informed decision making in research regarding chemical structures.

SUMMARY

According to an embodiment, a method includes receiving a domain specific language description of a chemical structure; converting the domain specific language description of the chemical structure into a graphical representation of the chemical structure; encoding the graphical representation of the chemical structure into a vector; and storing the vector into a searchable database. Other embodiments can include a computer system or a computer-readable storage media that perform the method.

DETAILED DESCRIPTION

Figure 1:
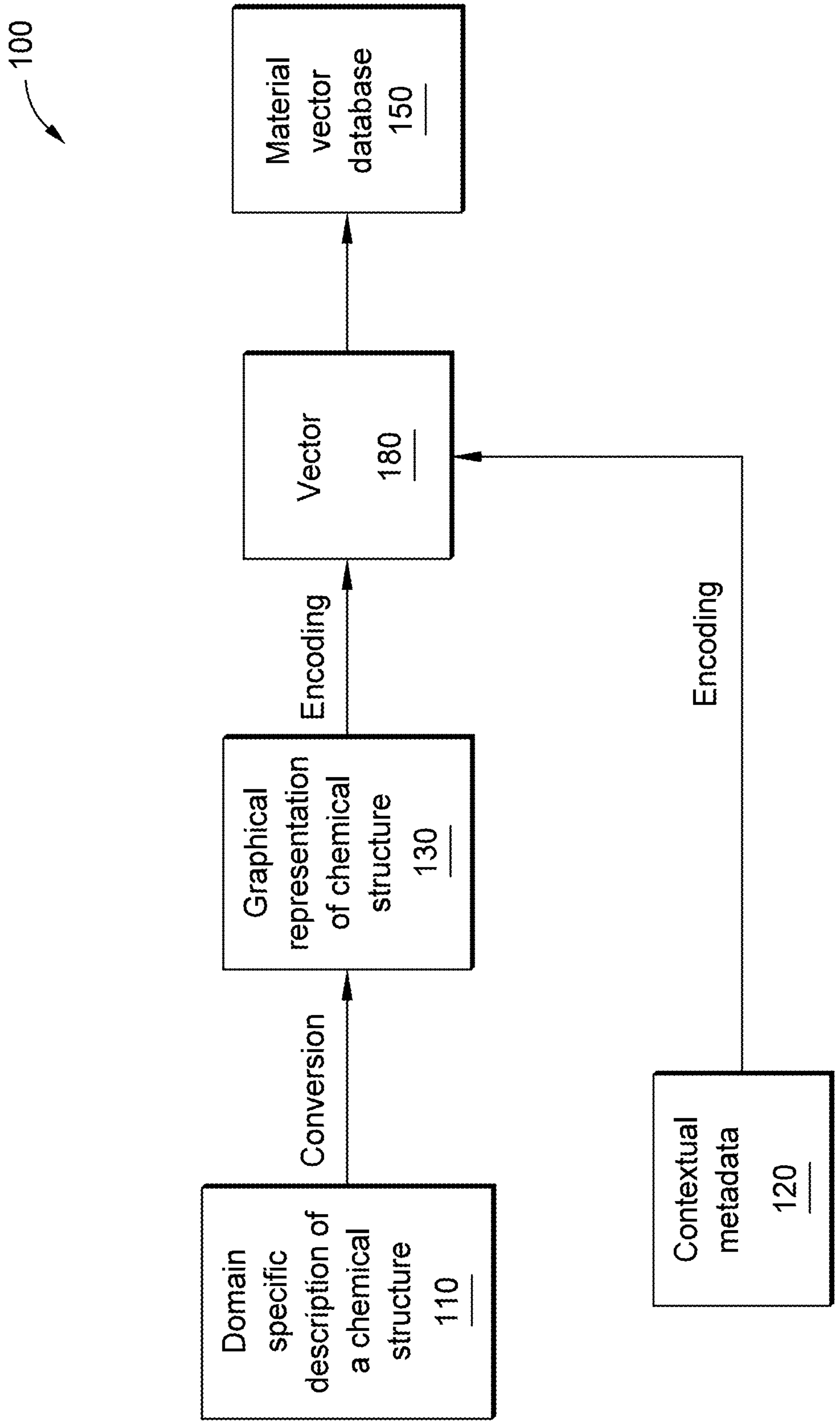
FIG. 1 illustrates an example operation performed by a computer system, according to some embodiments.

According to an embodiment, a method includes receiving a domain specific language description of a chemical structure; converting the domain specific language description of the chemical structure into a graphical representation of the chemical structure; encoding the graphical representation of the chemical structure into a vector; and storing the vector into a searchable database. By performing the method, various AI systems can utilize the comprehensive database, which is configured to store a robust amount of data regarding chemical structures.

Also in some embodiments, the method also includes receiving structural information for the chemical structure; and encoding the structural information into the vector. As a result, the vector represents the chemical structure more holistically.

Also in some embodiments of the, the domain specific language of the method indicates a function of the chemical structure, and where the function is encoded in the graphical representation. As a result, the vector represents the chemical structure more holistically.

Also in some embodiments, the graphical representation of the method includes a stochastic descriptor of the chemical structure. As a result, more depth and information is added to the vector representation of the chemical structure.

Also in some embodiments, the vector form the searchable database of method is accessed using at least one of: a multi-modal user query, a natural language query, or a built-in similarity search. As a result, the database can be used across multiple computer systems.

Also in some embodiments, the method also includes converting at least one of the multi-modal user query, the natural language query, or the built-in similarity search into a second graphical representation; encoding the second graphical representation of the query into a second vector; and using the second vector to access the first vector from the searchable database. As a result, the database can be searched effectively.

Also in some embodiments, the method also includes converting at least one of the multi-modal user query, the natural language query, or the built-in similarity search into the second graphical representation comprises translating at least one of the multi-modal user query, the natural language query, or the built-in similarity search using an LLM. As a result, the database can be searched effectively.

Also in some embodiments, the chemical structure of method includes a plurality of repeating units and bonds between the plurality of repeating units. As a result, the representation of the chemical structure is more holistic.

Also in some embodiments, converting the domain specific language description of the chemical structure into a graphical representation of the chemical structure of the method includes applying a machine learning model to the domain specific language description. As a result, analysis can be completed more efficiently.

According to another embodiment, a system includes: a processor set; one or more computer-readable storage media; and program instructions stored on one or more storage media to cause the processor set to perform operations including: receiving a domain specific language description of a chemical structure; converting the domain specific language description of the chemical structure into a graphical representation of the chemical structure; encoding the graphical representation of the chemical structure into a vector; and storing the vector into a searchable database. As a result, AI systems can utilize the comprehensive database, which is configured to store a robust amount of data regarding chemical structures.

Also in some embodiments, the system also includes receiving structural information for the chemical structure; and encoding the structural information into the vector. As a result, the vector represents the chemical structure more holistically.

Also in some embodiments, the domain specific language of the system indicates a function of the chemical structure, and where the function is encoded in the graphical representation. As a result, the vector represents the chemical structure more holistically.

Also in some embodiments, the graphical representation of the system includes a stochastic descriptor of the chemical structure. As a result, more depth and information is added to the vector representation of the chemical structure.

Also in some embodiments, the vector form the searchable database of the system is accessed using at least one of: a multi-modal user query, a natural language query, or a built-in similarity search. As a result, the database can be used across multiple computer systems.

Also in some embodiments, the system also includes converting at least one of the multi-modal user query, the natural language query, or the built-in similarity search into a second graphical representation; encoding the second graphical representation of the query into a second vector; and using the second vector to access the first vector from the searchable database. As a result, the database can be searched effectively.

Also in some embodiments, the system also includes converting at least one of the multi-modal user query, the natural language query, or the built-in similarity search into the second graphical representation comprises translating at least one of the multi-modal user query, the natural language query, or the built-in similarity search using an LLM. As a result, the database can be searched effectively.

Also in an embodiment, the chemical structure of the previously mentioned system includes a plurality of repeating units and bonds between the plurality of repeating units. As a result, the representation of the chemical structure is more holistic.

Also in some embodiments, converting the domain specific language description of the chemical structure into a graphical representation of the chemical structure of the system includes applying a machine learning model to the domain specific language description. As a result, analysis can be completed more efficiently. According to another embodiment, a computer program product for generating a database, the computer program product includes: one or more computer-readable storage media; and program instructions stored on one or more storage media to perform operations including: receiving a domain specific language description of a chemical structure; converting the domain specific language description of the chemical structure into a graphical representation of the chemical structure; encoding the graphical representation of the chemical structure into a vector; and storing the vector into a searchable database. As a result, various AI systems can utilize the comprehensive database, which is configured to store a robust amount of data regarding chemical structures.

Also in some embodiments, the computer program product operations further include: receiving structural information for the chemical structure; and encoding the structural information into the vector. As a result, the vector represents the chemical structure more holistically.

Embodiments herein relate to creating a database that can support natural language and multi-modal user queries regarding chemical structures. This database supports querying for polymer structure representations, among other types of chemical structures. Current chemical database systems face limitations when searching and representing polymer structures such as monomer substructures (or repeating units). Polymers tend to be large, complex molecules composed of repeating units (monomers), which pose challenges for database systems. Current systems have difficulty representing and searching for these repeating units and the varying chain lengths inherent to polymers. Databases may struggle to store polymers in a way that accurately reflects their structure and allows for efficient substructure searches. Furthermore, current systems may not adequately represent the connectivity and arrangement of monomer units, which can lead to inaccurate or incomplete search results.

The present disclosure describes a computer system that creates a material vector database that stores vector embeddings of chemical structures. The material vector database can provide a robust collection of data that supports a user query for complex chemical structures that currently are not supported. Such a database can be created using vector embeddings. Vector embeddings can be used to convert complex information, such as information regarding chemical structures, into dense, continuous vectors that encapsulate the features and relationships of the original data. This transformation provides an improvement in processing, analysis, and querying of the chemical structure data, including information regarding polymers. Transforming such complex data into vector embeddings makes querying the data and analyzing the data much more manageable. The vector embeddings can then create a material vector database. This enables multi-modal queries for polymers and other complex materials.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Figure 5:
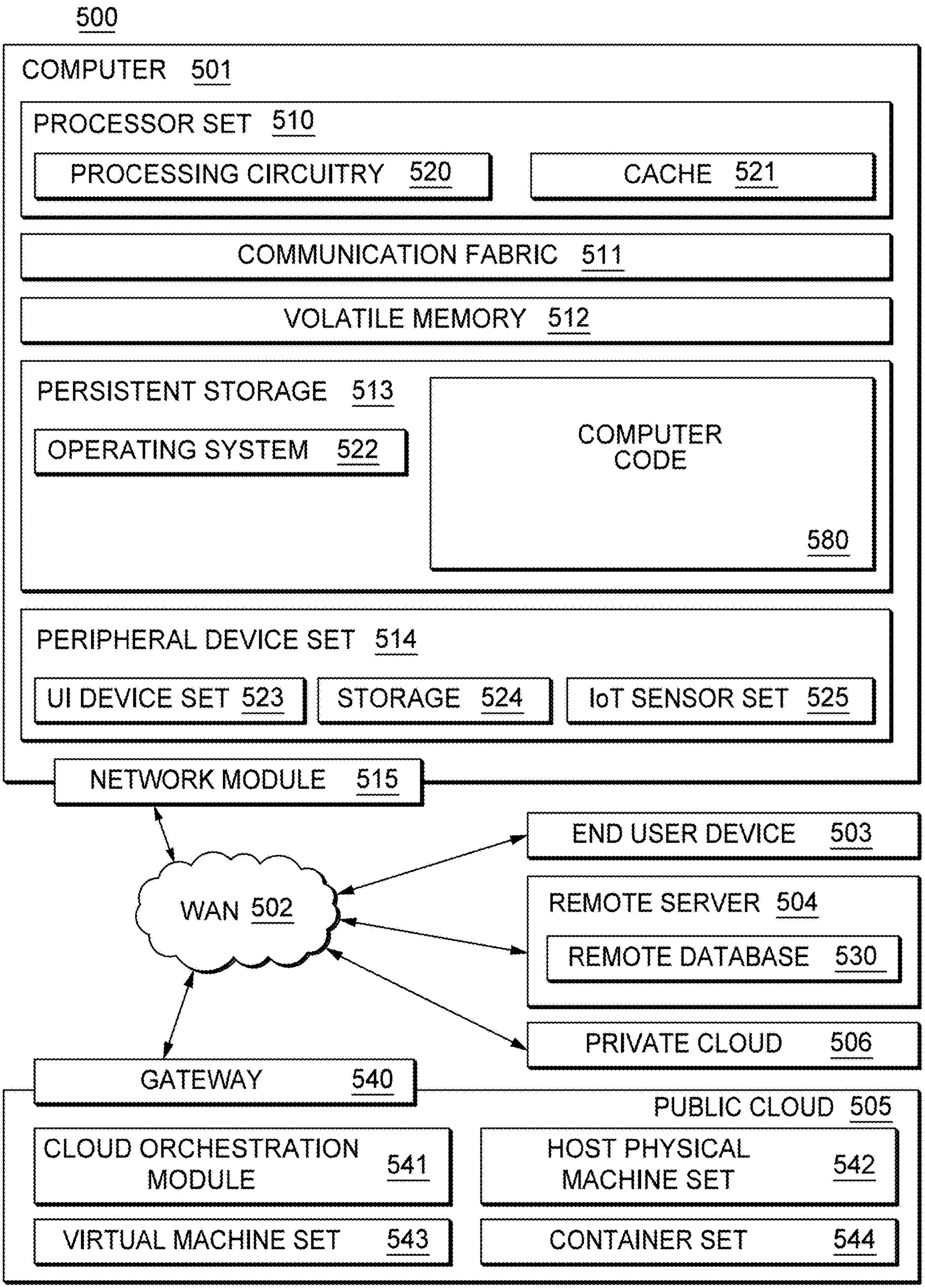
FIG. 5 illustrates a computing environment, according to some embodiments.

FIG. 1 illustrates an example operation 100, which may be performed by a computer system (e.g., the computer system 500 shown in FIG. 5). Generally, the computer system uses various techniques to generate a material vector database, enabling multi-modal queries for various chemical structures.

The computer system is presented with a domain specific description of a chemical structure 110. The domain specific description of a chemical structure 110 may be a Chemical Markdown Language (CMDL) file, or another domain specific language. Domain specific language descriptions refer to a specialized computer language designed to be effective for a specific domain or area of concern. Unlike general-purpose programming languages, which are designed to handle a wide range of applications, domain specific languages are tailored to provide specific features and notations that closely align with the tasks and problems of the particular domain. This focus enables users to express concepts and solutions more naturally and concisely within that domain. This improves the productivity and decreases the likelihood of errors.

There are different types of domain specific languages. One type is an internal domain specific language. Another type is an external domain specific language. Internal domain specific languages are built on top of existing general purpose languages, leveraging the syntax and features of the general purpose languages to create domain specific constructs. An example of this is SQL embedding within the general purpose Python code. External domain specific languages have their own distinct syntax and grammar, and use dedicated parsers and interpreters. An example of an external domain specific language is HTML, which is used for defining the structure of web pages.

An advantage of using a domain specific language is its ability to provide higher abstraction levels and/or intuitive notations for domain specific tasks. This leads to more readable, maintainable, and error resistant code, especially when used by domain experts who may not be professional programmers.

An example of a domain specific language in the context of chemistry is CMDL. CMDL is a specialized domain specific language designed for representing chemical information, using its own syntax do to so. CMDL allows chemical structures, reactions, properties and other related chemical information to be described in a machine readable format that can be easily processed by software tools.

CMDL is designed as a versatile domain specific language for documenting and representing experimental data in chemistry and materials science, with an emphasis on polymeric materials. The CMDL structure is built around two primary elements, being groups and properties. Groups organize related information under terms or keywords, allowing the representation of complex entities, such as chemicals, reactions, and experimental setups. Properties may be key-value pairs that may represent various types of data, including numerical values, text strings, lists, and references to other entities. This flexible structure enables CMDL to capture a wide range of chemical information, from simple molecular properties to complex polymer structures and reaction setups.

CMDL's structure includes built-in support for graph representations of polymeric structures and continuous flow reactors. This allows for a connection between these representation systems and experimental data. The language also supports references and nested structures, enabling the representation of complex relationships and hierarchies in chemical data. This comprehensive structure makes CMDL wells suited for merging disparate experimental data types and facilitating the development of machine learning models.

Benefits of CMDL include its ability to integrate diverse types of chemical data from different sources, and enabling interpretability between various chemical informatics systems. By providing a common framework for presenting chemical information, CMDL helps reduce data silos and promotes more effective data exchange and collaboration.

When the domain specific description of a chemical structure 110 (which may be a CMDL file) is received, the computer system converts the information from the received domain specific description of a chemical structure 110 into a graphical representation 130 of the chemical structure. The graphical representation 130 of the chemical structure may be a material graph with stochastic descriptors. A material graph with stochastic descriptors leverages graph theory to capture the complex relationships and interactions within a material's structure, while incorporating stochastic (probabilistic) descriptors to account for the inherent variability and uncertainty in material properties.

In a material graph, nodes may represent fundamental units of the material, such as atoms, molecules, or larger structural components, depending on the scale of interest. Edges between nodes may represent interactions or relationships, such as chemical bonds, physical forces or spatial proximity. By structuring a material in this way, a more detailed and holistic understanding of the material's properties and behaviors can be understood, enabling more accurate predictions and optimizations.

Stochastic descriptors add an additional layer of realism to a model by incorporating the probabilistic nature of material properties. These descriptors capture the statistical variations and uncertainties that arise from various sources, such as manufacturing processes, environmental conditions, and intrinsic material heterogeneity. For example, the strength of a bond between two atoms might not be a single fixed value, but rather a distribution of possible values based on experimental data or simulations.

Integrating stochastic descriptors into material graphs allows for more robust and comprehensive analyses. It enables the use of probabilistic methods to predict material performance under different conditions, assess reliability and risk, and optimize materials for specific applications. Material graphs with stochastic descriptors can facilitate advanced computational techniques such as machine learning and data driven modeling. By providing a rich and nuanced representation of material structures and properties, these models can be used to train algorithms that identify patterns, make predictions, and suggest novel materials with optimized characteristics, among other things.

Converting the domain specific description of a chemical structure 110 (such as a CMDL file) into a graphical representation 130 of a chemical structure (such as a material graph with stochastic descriptors) may be done in various ways. The process may involve extracting relevant chemical and structural data from the CMDL file, transforming the data into a graphical representation, and then integrating stochastic descriptors to account for variability and uncertainty in the material properties.

The computer system may parse the domain specific description of the chemical structure, such as a CMDL file, to identify and extract relevant chemical information.

Once data is extracted from the CMDL or domain specific language file, the construction of the material graph may commence. As previously mentioned, nodes may represent the basic units of the material, such as atoms or larger molecular structures, whereas edges may represent interactions or relationships between those units, such as chemical bonds or physical forces. Graph libraries, such as NetworkX in Python may facilitate the creation and manipulation of these graphs. The properties of the nodes and edges, such as atomic numbers, bond types, and spatial coordinates, may be assigned based on the data extracted from the CMDL file.

Incorporating stochastic descriptors into the material graph involves introducing probabilistic elements that capture the variability and uncertainty inherent in material properties. For example, the strength of a chemical bond might be represented not as a single value, but as a probability distribution based on experimental measurements or theoretical calculations, among other things. This can be achieved by attaching additional metadata to the nodes and edges of the graph, representing these probabilistic properties. Statistical methods or machine learning techniques can be employed to generate these descriptors from empirical data or simulations.

By converting a domain specific description of a chemical structure, such as a CMDL file, into a material graph with stochastic descriptors, the detailed chemical data encoded in the domain specific description, or CMDL file, as well as the powerful capabilities of graph theory and stochastic modeling can be leveraged. This may enhance the ability to design and optimize materials with tailored properties, supporting innovations in fields such as material science, nanotechnology, chemical engineering, etc.

The system encodes the graphical representation 130 of the chemical structure into a vector 180. Also encoded in the vector 180 is additional contextual metadata 120 for the chemical structure. Encoding information into the vector 180 involves transforming complex data into a structured numerical format that can be easily processed by machine learning algorithms and other computational models. The vector 180 may include an ordered list or an array of numbers where each number (or element) represents a certain feature or attribute of the data that is being encoded. This transformation enables efficient handling and analysis of data, facilitating tasks such as classification, clustering, prediction, and overall of diverse types of information.

The process of encoding may begin with identifying key features of the information that is to be captured. For instance, in the context of natural language processing, a sentence or document can be encoded into a vector where each element might represent the presence or frequency of a particular word, semantic meaning, or synthetic pattern. Similarly, in image processing, an image can be converted into a vector where each element corresponds to pixel intensity values or extracted features like edges and textures, among others. In the context of chemical structures, encoding may involve converting the molecular information into the vector 180, which captures key features, such as atom types, bond types, and molecular geometry. The encoding may be achieved through techniques like Morgan fingerprints or graph neural networks, which transform the chemical structure into a fixed length vector. The generated vector allows the encoded chemical information to be used as input for various machine learning models, facilitating tasks such as molecular property prediction, similarity search, and reaction outcome prediction, among other things.

Once features are identified, various techniques can be used to transform them into numerical values. This can involve simple mapping, such as one-hot encoding for categorical data, or more complex transformations such as word embeddings for text data, or principal component analysis (PCA) for dimensionality reduction. The resulting vector 180 preserves the characteristics of the original data while making it suitable for computational analysis. More information on encoding is discussed with FIG. 2.

Once the vector 180 is created, including information from both the graphical representation 130 of the chemical structure, as well as additional contextual metadata 120 of the chemical structure, the computer system stores the vector 180 in the material vector database 150. The material vector database 150 is a searchable database that contains other vectors of other chemical structures. The computer system creates the material vector database 150 by repeating the operation 100 to generate and store multiple vectors 180 for multiple chemical structures in the material vector database 150.

Figure 2:
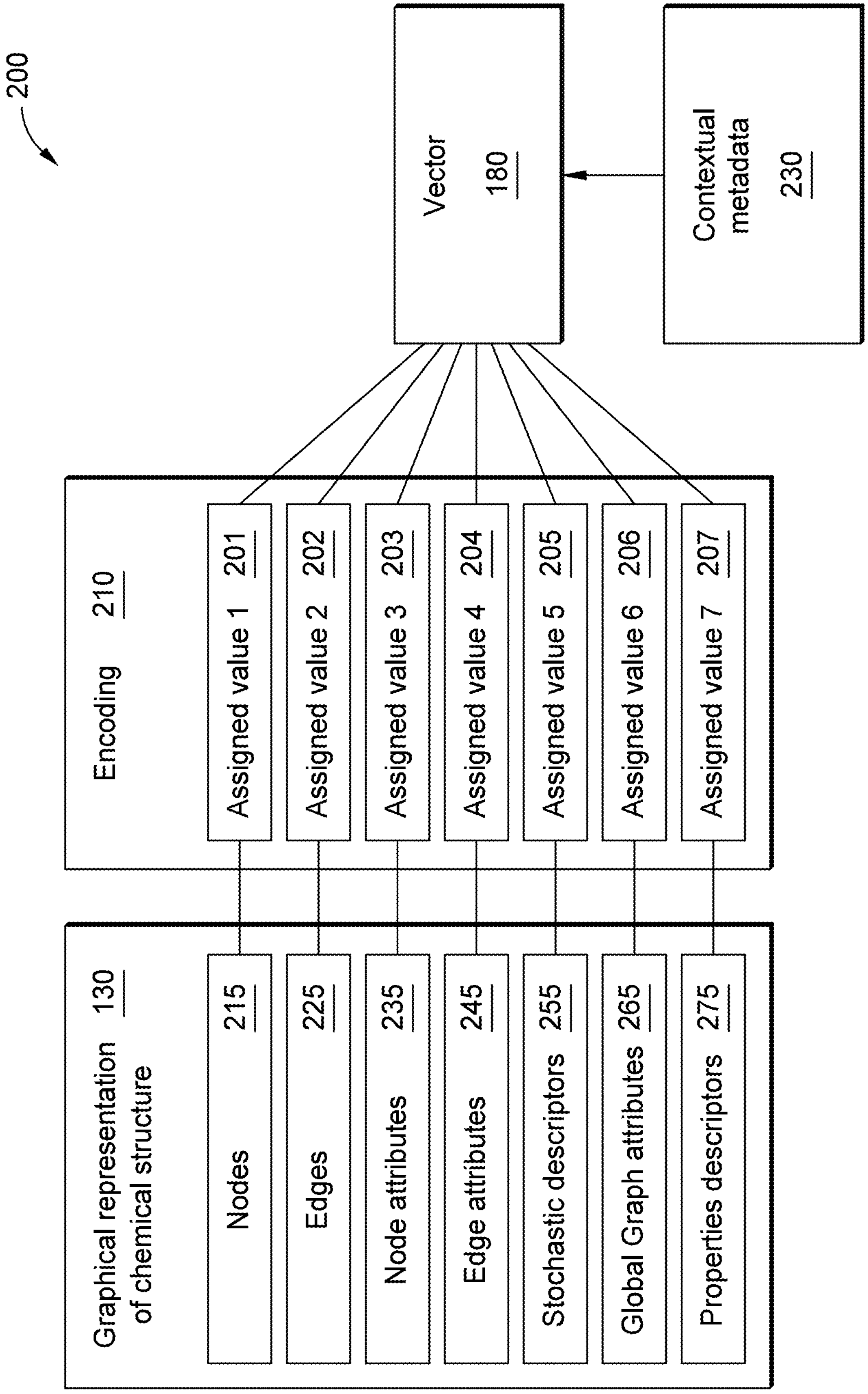
FIG. 2 illustrates an example operation performed by a computer system, according to some embodiments.

FIG. 2 illustrates an example operation 200 performed by a computer system (e.g., the computer system 500 shown in FIG. 5). Generally, the computer system generates a vector representing a chemical structure from a graphical representation of the chemical structure.

The graphical representation 130 of the chemical structure includes components that may be identified as important components of the chemical structure that should be encoded into the vector 180. Such components of the graphical representation 130 of the chemical structure include nodes 251, edges 225, node attributes 235, edge attributes 245, stochastic descriptors 255, global graph attributes 265, and properties descriptors 275. These are non-limiting examples of what information may be encoded.

The computer system generates an encoding 210 of the graphical representation 130. As seen in FIG. 2, the encoding 210 includes assigned values for the different components of the graphical representation 130.

The nodes 215 of the graphical representation 130 of the chemical structure may represent individual atoms, ions, molecules, etc. in the chemical structure. The computer system may encode the nodes 215 as an assigned value 201 and placed into the vector 180 as such.

The edges 225 of the graphical representation 130 of the chemical structure may represent links, such as bonds between atoms or interactions between molecules, nonbonding interactions such as van der Waals forces or hydrogen bonds, or distance metrics such as Euclidean distance or other metrics representing spatial relationships, among other things. The computer system may encode the edges 225 as an assigned value 202 and placed into the vector 180 as such.

The node attributes 235 of the graphical representation 130 of the chemical structure may represent the atomic number or each atom, the coordination number or the number or nearest neighbors or bonded atoms, the electric charge on each atom or ion, the atomic or molecular mass, spatial coordinates of the atoms in the material, properties such as electronegativity or ionization energy, or structural properties such as bond angles and lengths, among other attributes. The computer system may encode the node attributes 235 as an assigned value 203 and placed into the vector 180 as such.

The edge attributes 245 of the graphical representation 130 of the chemical structure may represent bond types such as a single, double, triple, or aromatic bonds, bond length, such as the distance between bonded atoms, bond strength such as the strength or energy associated with the bond, or interaction strength such as the strength of non-bonding interactions, among other things. The computer system may encode the edge attributes 245 as an assigned value 204 and placed into the vector 180 as such.

The stochastic descriptors 255 of the graphical representation 130 of the chemical structure may represent disorder parameters or measurements of the disorder or randomness in the material structure (e.g., atomic displacement parameters), probabilistic distributions such as statistical distributions of properties like bond lengths, angles, and coordination numbers, uncertainty measures such as quantifications of uncertainties in material properties due to stochastic variations, random fields such as mathematical functions representing spatially varying random properties, Monte Carlo samples such as simulated samples representing possible variations in the material properties, or statistical moments such as mean, variance skewness and kurtosis of property distributions, among other things. The computer system may encode the stochastic descriptors 255 as an assigned value 205 and placed into the vector 180 as such.

The global graph attributes 265 of the graphical representation 130 of the chemical structure may represent temperature, such as the temperature at which the material properties are considered, pressures such as the pressure conditions affecting the material, environmental conditions such as humidity, pH, etc., crystalline symmetry such as the symmetry properties of crystal structures, or phase information such as information about different phases of the present material, among other things. The computer system may encode the global graph attributes 265 as an assigned value 206 and placed into the vector 180 as such.

The properties descriptors 275 of the graphical representation 130 of the chemical structure may represent mechanical properties such as stochastic variations in mechanical properties like elasticity, hardness, and tensile strength, thermal properties such as variability in thermal conductivity, specific heat and thermal expansion, electrical properties such as stochastic aspects of electrical conductivity, optical properties such as variations in optical properties like refractive index, absorption, and reflectivity, and chemical properties such as stochasticity in reactivity, corrosion resistance and chemical stability, among other things. The computer system may encode the properties descriptors 275 as an assigned value 207 and placed into the vector 180 as such.

Additionally, the computer system may encode the additional contextual metadata 120 beyond what is found in the graphical representation 130 of the chemical structure in the vector 180. This additional contextual metadata 120 for the chemical structure or characterization data may help add more detail to the domain specific description of the chemical structure 110.

Metadata is data that provides information about other data. It may serve as a descriptor, offering context and details to help understand and manage the data it describes. Metadata can include various types of information, such as the data's origin, structure, format and usage. Common types of metadata include but are not limited to descriptive metadata, structural metadata, and administrative metadata. Descriptive metadata provides information to identify and describe a resource. This can include titles, authors, dates, keywords, etc. Structural metadata indicates how the data is organized. For example, it can describe the structure of a dataset, the relationships between different parts of the data, or the format of the data, among other things. Administrative metadata offers information to help manage a resource, such as a file type, creation date, permissions, and access rights. Metadata helps with data management, retrieval, and usability. It can help locate, understand and maintain data efficiency. For example, in a digital library, metadata about a book includes the title, author, publication data, and subject keywords, among other things, enabling users to find and access the book easily.

Characterization data about a chemical structure in the form of metadata provides descriptive and contextual information that aids in understanding and utilizing the chemical structure effectively. The metadata encompasses various types of information that describes the properties, behavior, and context of the chemical entity, ensuring that users can accurately interpret and apply the data in their research or applications.

Structural metadata about a chemical structure may include details about the molecular composition and connectivity of the atoms within the molecule(s). This may involve information such as the chemical formula, molecular weight, and stereochemistry, among other things. For example, metadata might specify that a molecule has a certain molecular formula, which indicates the presence of a certain number of different types of atoms. It may also include data on bond types and the spatial arrangement of atoms, among other things.

Another aspect of characterization metadata includes the spectroscopic and physical properties of the chemical structure. This includes but is not limited to data obtained from various spectroscopic techniques such as nuclear magnetic resonance (NMR), infrared spectroscopy (IR), ultraviolet-visible spectroscopy (UV-Vis), mass spectrometry and more. For example, NMR metadata might provide chemical shift values, coupling constants, and information about the multiplicity of signals, etc., which are valuable for elucidating the molecular structure. Physical properties like melting point, boiling point, density, solubility, and refractive index, among other things, may be included and may provide a comprehensive profile of the compound's physical characteristics.

Also, in cheminformatics, computational and theoretical data play a role in the characterization of chemical structures. Metadata in this category include results from computational chemistry methods such as quantum mechanical calculations and molecular dynamics simulations. This data can provide insights into the electronic structure, and potential energy surfaces, optimized geometries, and predicted reactivity of a molecule. For example, metadata might detail the calculated highest occupied molecular orbital (HOMO), and lowest unoccupied molecular orbital (LUMO) energies, which may help with understanding the molecule's properties and behavior in chemical reactions.

Additionally, contextual and experimental metadata provides information about the conditions under which the chemical structure was studied or synthesized. This includes details about the experimental setup, such as temperature, pressure, solvents used, and certain methods employed for synthesis and analysis. Metadata may also include references to publications, or datasets where the chemical structure has been reported or utilized. This contextual information helps with reproducibility and with understanding the applicability and limitations of the data.

Characterization data about a chemical structure in the form of metadata provides a multifaceted description that enhances the usability, interpretability, and reproducibility of chemical information. It helps ensure access to comprehensive and detailed information about the chemical structure, facilitating more informed and accurate analysis and decision making.

Combining the additional contextual metadata 120, which can be additional metadata, with the graphical representation 130 of the chemical structure to produce the vector 180, allows for a more comprehensive representation of the chemical structure, as the vector 180 will contain structural and contextual details of the molecule.

The graphical representation 130 of the chemical structure may depict the arrangement of atoms and bonds within the molecule, providing a visual map of its molecular geometry. The additional contextual metadata 120, which may be additional metadata, offers descriptive information such as chemical formula, molecular weight, spectroscopic data, physical properties, and computational predictions. By integrating these two forms of information in the vector 180, a more holistic representation of the molecule may be created. For example, while the graphical representation 130 shows the spatial arrangement and connectivity, the additional contextual metadata 120 adds layers of context, such as the experimental conditions under which the molecule was studied, among other things.

To encode the combined information into a vector, both the graphical representation 130 and the additional contextual metadata 120, should be encoded into numerical features that machine learning models or other computational systems can process. As previously discussed, for the graphical representation 130, this may involve encoding the molecular structure using techniques like molecular fingerprints or graph embeddings, which translate the 2-dimensional or 3-dimensional molecular structure into a numerical vector. The elements of the vector, such as vector 180, may represent certain features such as the presence of certain functional groups, the number of rings, or certain bond types.

Simultaneously, the computer system also converts the additional contextual metadata 120 into numerical form. Descriptive data, such as molecular weight, boiling point, or NMR chemical shifts can be directly encoded as vector elements. Categorical data such as solvent type, experimental conditions, etc., can be transformed using one-hot encoding or similar techniques.

The encoded information from both the additional contextual metadata 120 and the graphical representation 130 make up the vector 180. This comprehensive vector 180 offers several advantages. It enables machine learning models or other computer systems to leverage both the structural and contextual information, improving the accuracy and relevance of predictions in tasks such as property prediction, activity modeling, and molecular similarity searches. The vector 180 enables more nuanced and effective computational analysis of chemical structures, bridging the gap between visual molecular representations and qualitative data, enabling more advanced applications.

Figure 3:
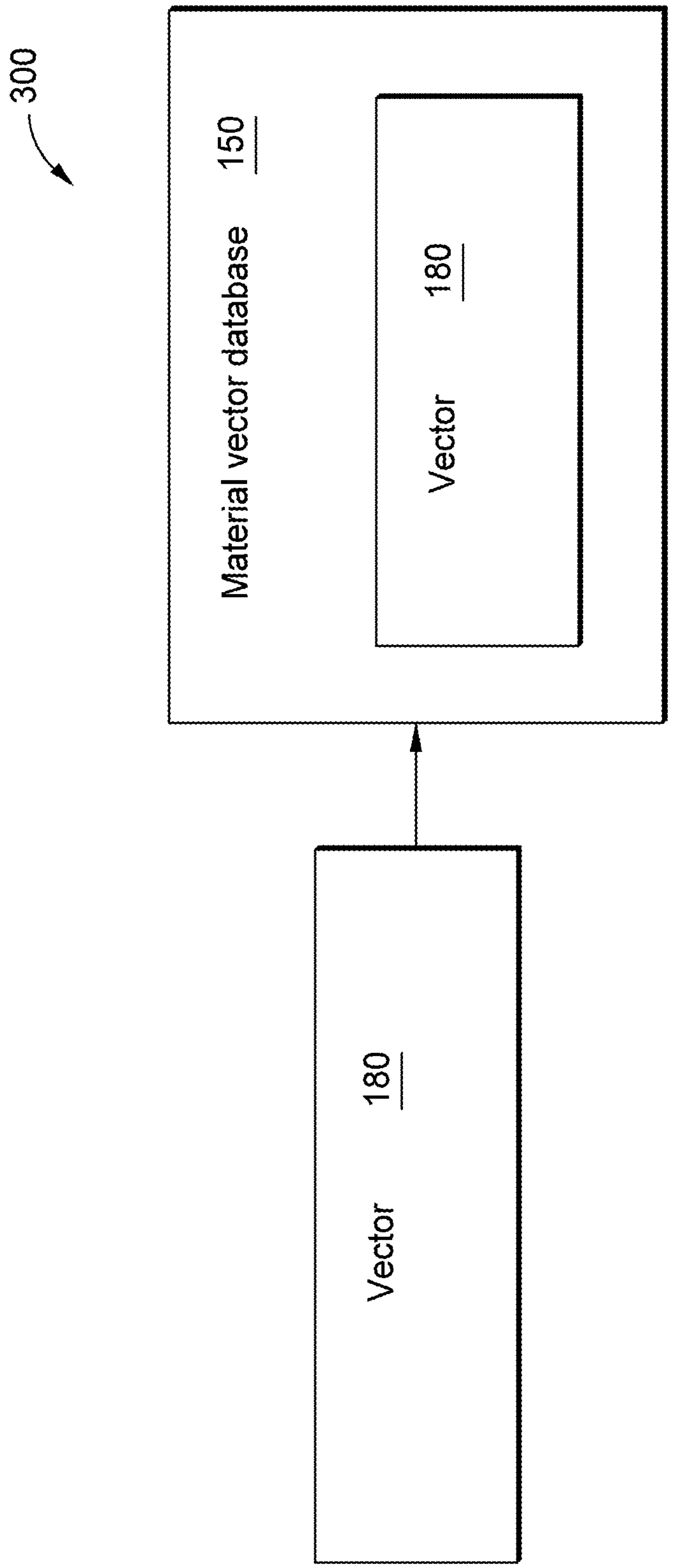
FIG. 3 illustrates an example operation performed by a computer system, according to some embodiments.

FIG. 3 illustrates an example operation 300, which may be performed by a computer system (e.g., the computer system 500 shown in FIG. 5). Generally, the computer system stores the vector 180 in the material vector database 150. The material vector database 150 can support natural language and multi-modal queries, provide built in similarity search, and therefore enhance retrieval augmented generation (RAG) accuracy as well as material design tasks.

When a database, such as the material vector database 150, can support natural language queries, it means that users can interact with the database using everyday language rather than certain query languages or complex search parameters. This capability leverages natural language processing techniques to interpret and translate user input into structured queries that the database can understand and execute.

When a database, such as the material vector database 150, supports multi-modal queries, users are able to retrieve and interact with data using multiple formats of input. Multiple formats of input include but are not limited to text, images, audio, and video. For example, in a multi-modal database such as the material vector database 150, a user could submit a chemical structure diagram along with a textual description. The system could process both the visual and textual components of the query, integrate the relevant data, and return results from the database that meet the criteria specified across the different modalities. This enhances the database's usability, enabling more nuanced and sophisticated searches that can draw on diverse types of data for richer insights and more precise results.

When a database, such as the material vector database 150, provides built in similarity searches, it means the database includes functionalities that allow users to find entries that are similar to a given query. This is useful when attempting to identify items that share certain characteristics or features. The material vector database 150 may be searched using a multi-modal user query, a natural language query, or a built-in similarity search. These queries may be converted into graphical representations, and then vectors for information retrieval purposes. A query may be in textual form, and when transformed into a graphical form, elements of the query can be treated as nodes and their relationships as edges. Once a query is represented as a graph, the graphical representation can be converted into a vector. This conversion process may include embedding nodes and edges into a continuous vector space using techniques such as graph neural networks (GNNs), graph embeddings, etc. These techniques, among others, can learn to represent the graph in a high-dimensional space where similar structures are close to each other. The resulting vector may then encapsulate the semantic meaning and relationships within the query, making it suitable for computational analysis and comparison. The query vector may be used to search the material vector database 150. The query vector may be compared against vectors in the database using similarity measures, such as cosine similarity or Euclidean distance, where vectors from the material vector database 150 can be retrieved based on similarity to the query vector.

Additionally, a large language model (LLM) can facilitate the process of converting queries into graphical representations and transforming such representations into vectors. An LLM can also facilitate the comparison of the query vector with vectors in the database using similarity measures. The LLM may effectively manage the process form query conversion to vector search.

The material vector database 150 is not limited to the above mentioned capabilities. The material vector database 150 incorporate improvements that enhance retrieval augmented generation (RAG) accuracy as well as material design tasks, among other things.

Figure 4:
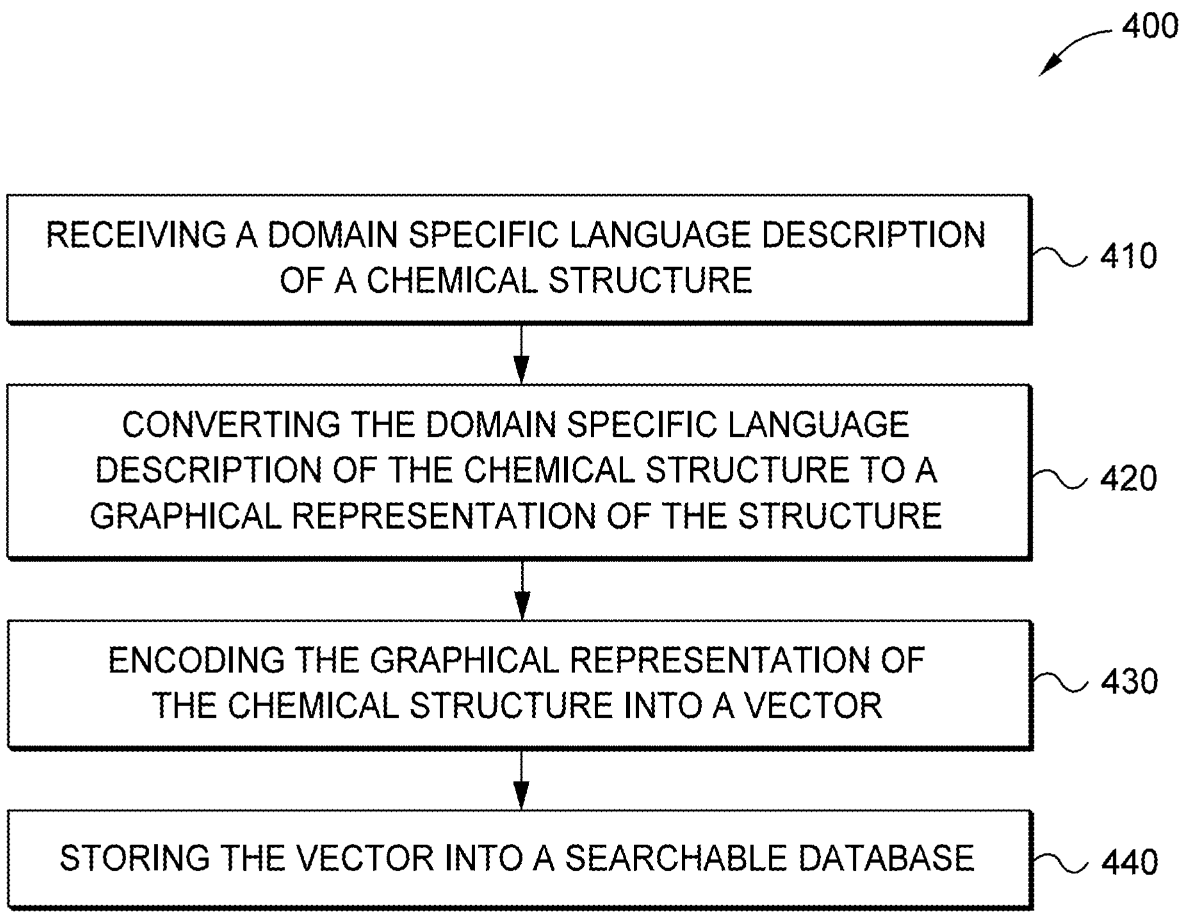
FIG. 4 is a flowchart of an example method performed by a computer system, according to some embodiments.

FIG. 4 is a flowchart of an example method 400 performed by a computer system (e.g., the computer system 500 shown in FIG. 5). Generally, by performing the method 400, the computer system generates and stores vectors representing chemical structures.

At block 410, the computer system receives a domain specific language description of a chemical structure. As previously mentioned, this domain specific language description may be a CMDL file. There are many types of domain specific languages, and they offer advantages by providing tailored syntax and features optimized for specific fields, enhancing productivity and reducing complexity. They allow expressing concepts and operations more naturally and concisely within their domain, leading to more efficient development, easier maintenance, and fewer errors. Additionally, domain specific languages can improve communication and collaboration by using terminology and abstractions familiar to the field.

At block 420, the computer system converts the domain specific language description of the chemical structure to a graphical representation of the structure. Converting a domain specific language description of a chemical structure into a graphical representation of the chemical structure can bolster usability, interpretation, and communication of chemical information, among other things. For example, a graphical representation of a chemical structure can enhance the visualization of molecular structures. While textual descriptions in a domain specific language provide precise and detailed information, they can be challenging to interpret at a glance. Graphical representations, on the other hand, offer an intuitive and easily interpretable view of the chemical structure, allowing chemists to quickly understand the molecular geometry, bond relationships, and functional groups, among other things, present in the molecule. This visual approach facilitates more efficient analysis and comprehension of chemical data.

A graphical representation of a chemical structure includes nodes and edges that may symbolize atoms and bonds respectively. The nodes in the graph may correspond to atoms in a molecule, and the type of atom may be identified by a label, color, etc. The edges may represent the chemical bonds between the atoms, where single, double, and triple bonds may be depicted by one, two or three lines respectively. Additionally, graphical representations may include information about the three-dimensional arrangement of atoms, using dashed or wedged lines to indicate bonds that extend below or above the plane of paper. The components of a graphical representation offer informed visualizations of chemical structures.

At block 430, the computer system encodes the information from the graphical representation of the chemical structure into a vector. As discussed above, this step involves representing the elements of the graph in numeric form. The purpose of encoding is to transform data into a structured format that can be more easily processed, analyzed and interpreted by computational systems. Encoding enables the conversion of complex information, such as textual descriptions, images, or other forms of data into numerical or standardized formats that machine learning algorithms and other data processing tools can effectively handle. This transformation allows for efficient storage, retrieval, and manipulation of data, facilitating tasks such as pattern recognition, classification and prediction. Encoding data enables leveraging advanced computational techniques to extract valuable insights, make informed decisions, and automate various processes across diverse applications.

Encoding may be referred to as molecular feature generation or feature extraction. It translates the structural and chemical information of molecules into numerical formats that can be used for various computational tasks, such as machine learning, similarity searches, and quantitative structure-activity relationship (QSAR) modeling, among other things.

A non-limiting example of encoding includes representing the graphical representation with adjacency matrices or incidence matrices, which capture the connectivity between atoms. An adjacency matrix is a square matrix where the elements represent the presence or absence of a bond between two atoms. This matrix can be further enriched by incorporating the type of bond (e.g., single, double, triple) and the types of atoms involved, thus adding more granularity to the representation. From this matrix, a numerical vector can be derived. The descriptors in the matrix help quantify aspects such as atom counts, bond counts, molecular weight, and topological indices.

Another non-limiting example of encoding involves the use of molecular fingerprints. Fingerprints are bit strings or arrays that encode the presence or absence of certain substructures or features within a molecule. Techniques such as extended connectivity fingerprints (ECFP) of the molecular access system (MACCS) keys transform a molecule into a binary vector where each bit represents the presence of a certain sub structural feature. Fingerprints provide a compact and efficient way to encode complex molecular information.

Additionally, graph neural networks (GNNs) can also be used to encode molecular structures. GNNs treat molecules as graphs, where nodes may represent atoms and edges may represent bonds. These networks can encode the graph's structure into continuous numerical vectors, capturing more intricate patterns and properties. By training on large datasets, GNNs can develop sophisticated representations that consider both logical and global features of the molecule, leading to improved predictions in tasks such as property prediction, activity prediction, and virtual screening.

At block 440, the computer system stores the vector in a searchable database. As previously mentioned, the searchable database may contain other vectors pertaining to other chemical structures. The database may include functionality that makes information retrieval and use efficient, enabling more advanced data analysis, among other advantages.

In the preceding, reference is made to embodiments presented in this disclosure. However, the scope of the present disclosure is not limited to specific described embodiments. Instead, any combination of the features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the aspects, features, embodiments and advantages discussed herein are merely illustrative and are not considered elements or limitations of the appended claims except where explicitly recited in a claim(s).

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system."

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

FIG. 5 illustrates an example computing environment 500, which contains an example of an environment for the execution of at least some of the computer code involved in performing the inventive methods, such as the computer code 580, which stores encoded information regarding a chemical stricture. In addition to block 580, computing environment 500 includes, for example, computer 501, wide area network (WAN) 502, end user device (EUD) 503, remote server 504, public cloud 505, and private cloud 506. In this embodiment, computer 501 includes processor set 510 (including processing circuitry 520 and cache 521), communication fabric 511, volatile memory 512, persistent storage 513 (including operating system 522 and block 580, as identified above), peripheral device set 514 (including user interface (UI) device set 523, storage 524, and Internet of Things (IoT) sensor set 525), and network module 515. Remote server 504 includes remote database 530. Public cloud 505 includes gateway 540, cloud orchestration module 541, host physical machine set 542, virtual machine set 543, and container set 544.

COMPUTER 501 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 530. As is well understood in the art of computer technology, and depending upon the technology, performance of a computer-implemented method may be distributed among multiple computers and/or between multiple locations. On the other hand, in this presentation of computing environment 500, detailed discussion is focused on a single computer, specifically computer 501, to keep the presentation as simple as possible. Computer 501 may be located in a cloud, even though it is not shown in a cloud in FIG. 5. On the other hand, computer 501 is not required to be in a cloud except to any extent as may be affirmatively indicated.

PROCESSOR SET 510 includes one, or more, computer processors of any type now known or to be developed in the future. Processing circuitry 520 may be distributed over multiple packages, for example, multiple, coordinated integrated circuit chips. Processing circuitry 520 may implement multiple processor threads and/or multiple processor cores. Cache 521 is memory that is located in the processor chip package(s) and is typically used for data or code that should be available for rapid access by the threads or cores running on processor set 510. Cache memories are typically organized into multiple levels depending upon relative proximity to the processing circuitry. Alternatively, some, or all, of the cache for the processor set may be located "off chip." In some computing environments, processor set 510 may be designed for working with qubits and performing quantum computing.

Computer readable program instructions are typically loaded onto computer 501 to cause a series of operational steps to be performed by processor set 510 of computer 501 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 521 and the other storage media discussed below. The program instructions, and associated data, are accessed by processor set 510 to control and direct performance of the inventive methods. In computing environment 500, at least some of the instructions for performing the inventive methods may be stored in block 580 in persistent storage 513.

COMMUNICATION FABRIC 511 is the signal conduction path that allows the various components of computer 501 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 512 is any type of volatile memory now known or to be developed in the future. Examples include dynamic type random access memory (RAM) or static type RAM. Typically, volatile memory 512 is characterized by random access, but this is not required unless affirmatively indicated. In computer 501, the volatile memory 512 is located in a single package and is internal to computer 501, but, alternatively or additionally, the volatile memory may be distributed over multiple packages and/or located externally with respect to computer 501.

PERSISTENT STORAGE 513 is any form of non-volatile storage for computers that is now known or to be developed in the future. The non-volatility of this storage means that the stored data is maintained regardless of whether power is being supplied to computer 501 and/or directly to persistent storage 513. Persistent storage 513 may be a read only memory (ROM), but typically at least a portion of the persistent storage allows writing of data, deletion of data and re-writing of data. Some familiar forms of persistent storage include magnetic disks and solid state storage devices. Operating system 522 may take several forms, such as various known proprietary operating systems or open source Portable Operating System Interface-type operating systems that employ a kernel. The code included in block 580 typically includes at least some of the computer code involved in performing the inventive methods.

PERIPHERAL DEVICE SET 514 includes the set of peripheral devices of computer 501. Data communication connections between the peripheral devices and the other components of computer 501 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments, UI device set 523 may include components such as a display screen, speaker, microphone, wearable devices (such as goggles and smart watches), keyboard, mouse, printer, touchpad, game controllers, and haptic devices. Storage 524 is external storage, such as an external hard drive, or insertable storage, such as an SD card. Storage 524 may be persistent and/or volatile. In some embodiments, storage 524 may take the form of a quantum computing storage device for storing data in the form of qubits. In embodiments where computer 501 is required to have a large amount of storage (for example, where computer 501 locally stores and manages a large database) then this storage may be provided by peripheral storage devices designed for storing very large amounts of data, such as a storage area network (SAN) that is shared by multiple, geographically distributed computers. IoT sensor set 525 is made up of sensors that can be used in Internet of Things applications. For example, one sensor may be a thermometer and another sensor may be a motion detector.

NETWORK MODULE 515 is the collection of computer software, hardware, and firmware that allows computer 501 to communicate with other computers through WAN 502. Network module 515 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 515 are performed on the same physical hardware device. In other embodiments (for example, embodiments that utilize software-defined networking (SDN)), the control functions and the forwarding functions of network module 515 are performed on physically separate devices, such that the control functions manage several different network hardware devices. Computer readable program instructions for performing the inventive methods can typically be downloaded to computer 501 from an external computer or external storage device through a network adapter card or network interface included in network module 515.

WAN 502 is any wide area network (for example, the internet) capable of communicating computer data over non-local distances by any technology for communicating computer data, now known or to be developed in the future. In some embodiments, the WAN 502 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 503 is any computer system that is used and controlled by an end user (for example, a customer of an enterprise that operates computer 501), and may take any of the forms discussed above in connection with computer 501. EUD 503 typically receives helpful and useful data from the operations of computer 501. For example, in a hypothetical case where computer 501 is designed to provide a recommendation to an end user, this recommendation would typically be communicated from network module 515 of computer 501 through WAN 502 to EUD 503. In this way, EUD 503 can display, or otherwise present, the recommendation to an end user. In some embodiments, EUD 503 may be a client device, such as thin client, heavy client, mainframe computer, desktop computer and so on.

REMOTE SERVER 504 is any computer system that serves at least some data and/or functionality to computer 501. Remote server 504 may be controlled and used by the same entity that operates computer 501. Remote server 504 represents the machine(s) that collect and store helpful and useful data for use by other computers, such as computer 501. For example, in a hypothetical case where computer 501 is designed and programmed to provide a recommendation based on historical data, then this historical data may be provided to computer 501 from remote database 530 of remote server 504.

PUBLIC CLOUD 505 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 505 is performed by the computer hardware and/or software of cloud orchestration module 541. The computing resources provided by public cloud 505 are typically implemented by virtual computing environments that run on various computers making up the computers of host physical machine set 542, which is the universe of physical computers in and/or available to public cloud 505. The virtual computing environments (VCEs) typically take the form of virtual machines from virtual machine set 543 and/or containers from container set 544. It is understood that these VCEs may be stored as images and may be transferred among and between the various physical machine hosts, either as images or after instantiation of the VCE. Cloud orchestration module 541 manages the transfer and storage of images, deploys new instantiations of VCEs and manages active instantiations of VCE deployments. Gateway 540 is the collection of computer software, hardware, and firmware that allows public cloud 505 to communicate through WAN 502.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 506 is similar to public cloud 505, except that the computing resources are only available for use by a single enterprise. While private cloud 506 is depicted as being in communication with WAN 502, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 505 and private cloud 506 are both part of a larger hybrid cloud.

CLOUD COMPUTING SERVICES AND/OR MICROSERVICES (not separately shown in FIG. 1): private and public clouds 106 are programmed and configured to deliver cloud computing services and/or microservices (unless otherwise indicated, the word "microservices" shall be interpreted as inclusive of larger "services" regardless of size). Cloud services are infrastructure, platforms, or software that are typically hosted by third-party providers and made available to users through the internet. Cloud services facilitate the flow of user data from front-end clients (for example, user-side servers, tablets, desktops, laptops), through the internet, to the provider's systems, and back. In some embodiments, cloud services may be configured and orchestrated according to as "as a service" technology paradigm where something is being presented to an internal or external customer in the form of a cloud computing service. As-a-Service offerings typically provide endpoints with which various customers interface. These endpoints are typically based on a set of APIs. One category of as-a-service offering is Platform as a Service (PaaS), where a service provider provisions, instantiates, runs, and manages a modular bundle of code that customers can use to instantiate a computing platform and one or more applications, without the complexity of building and maintaining the infrastructure typically associated with these things. Another category is Software as a Service (Saas) where software is centrally hosted and allocated on a subscription basis. SaaS is also known as on-demand software, web-based software, or web-hosted software. Four technological sub-fields involved in cloud services are: deployment, integration, on demand, and virtual private networks.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present disclosure, other and further embodiments may be devised without departing from the basic scope thereof, and the scope thereof is determined by the claims that follow.

What is claimed is:

1. A method comprising:

receiving, by a computer system, a domain specific language description of a chemical structure;

converting, by the computer system, the domain specific language description of the chemical structure into a graphical representation of the chemical structure;

applying a machine learning model to the domain specific language description;

encoding the graphical representation of the chemical structure into a vector comprising a plurality of numbers by determining a value for each feature of the graphical representation, wherein the plurality of numbers in the vector comprises a number for each feature of the graphical representation, and wherein the value for each feature comprises at least one of: one-hot encoding, word embeddings, or principal component analysis, wherein encoding the graphical representation further comprises:

receiving contextual metadata for the chemical structure;

encoding the contextual metadata into numerical form; and combining the contextual metadata with the graphical representation of the chemical structure into the vector, wherein the vector transforms the contextual metadata and the graphical representation of the chemical structure into a structured format, storing, by the computer system, the vector into a multi-modal searchable database;

accessing, by the computer system, the multi-modal searchable database based on the structured format for processing the vector by the machine learning model;

converting at least one of the multi-modal user query, the natural language query, or the built-in similarity search into a second graphical representation;

encoding the second graphical representation of the query into a second vector; and using the second vector to access the vector from the multi-modal database.

2. The method of claim 1, further comprising:

receiving structural information for the chemical structure; and encoding the structural information into the vector; and wherein the contextual metadata comprises at least one of descriptive metadata, experimental metadata, structural metadata, or administrative metadata.

3. The method of claim 1, wherein the domain specific language description indicates a function of the chemical structure, and wherein the function is encoded in the graphical representation.

4. The method of claim 1, wherein the graphical representation comprises a stochastic descriptor of the chemical structure.

5. The method of claim 1, wherein the method further comprises accessing the vector from the multi-modal database using a multi-modal user query, and wherein the multimodal database is further configured to access the vector using at least one of:

a natural language query, or a built-in similarity search.

6. The method of claim 5, wherein converting at least one of the multi-modal user query, the natural language query, or the built-in similarity search into the second graphical representation comprises translating at least one of the multi-modal user query, the natural language query, or the built-in similarity search using an LLM.

7. The method of claim 1 wherein the chemical structure comprises a plurality of repeating units and bonds between the plurality of repeating units.

8. A system comprising:

a processor set;

one or more computer-readable storage media; and program instructions stored on one or more storage media to cause the processor set to perform operations comprising:

receiving, by a computer system, a domain specific language description of a chemical structure;

converting, by the computer system, the domain specific language description of the chemical structure into a graphical representation of the chemical structure;

applying a machine learning model to the domain specific language description;

encoding the graphical representation of the chemical structure into a vector comprising a plurality of numbers by determining a value for each feature of the graphical representation, wherein the plurality of numbers in the vector comprises a number for each feature of the graphical representation, and wherein the value for each feature comprises at least one of: one-hot encoding, word embeddings, or principal component analysis, wherein encoding the graphical representation further comprises:

receiving contextual metadata for the chemical structure;

encoding the contextual metadata into numerical form; and combining the contextual metadata with the graphical representation of the chemical structure into the vector, wherein the vector transforms the contextual metadata and the graphical representation of the chemical structure into a structured format, storing, by the computer system, the vector into a multi-modal searchable database;

accessing, by the computer system, the multi-modal searchable database based on the structured format for processing the vector by the machine learning model;

converting at least one of the multi-modal user query, the natural language query, or the built-in similarity search into a second graphical representation;

encoding the second graphical representation of the query into a second vector; and using the second vector to access the vector from the multi-modal database.

9. The system of claim 8, wherein the operations further comprise:

receiving structural information for the chemical structure; and encoding the structural information into the vector; and wherein the contextual metadata comprises at least one of descriptive metadata, experimental metadata, structural metadata, or administrative metadata.

10. The system of claim 8, wherein the domain specific language description indicates a function of the chemical structure, and wherein the function is encoded in the graphical representation.

11. The system of claim 8, wherein the graphical representation comprises a stochastic descriptor of the chemical structure.

12. The system of claim 8, wherein the operations further comprises accessing the vector from the multi-modal database using a multi-modal user query, and wherein the multi-modal database is further configured to access the vector using at least one of:

a natural language query, or a built-in similarity search.

13. The system of claim 12, wherein converting at least one of the multimodal user query, the natural language query, or the built-in similarity search into the second graphical representation comprises translating at least one of the multi-modal user query, the natural language query, or the built-in similarity search using an LLM.

14. The system of claim 8, wherein the chemical structure comprises a plurality of repeating units and bonds between the plurality of repeating units.

15. A computer program product for generating a database, the computer program product comprising:

one or more non-transitory computer-readable storage media; and program instructions stored on one or more storage media to perform operations comprising:

receiving, by a computer system, a domain specific language description of a chemical structure;

converting, by the computer system, the domain specific language description of the chemical structure into a graphical representation of the chemical structure;

applying a machine learning model to the domain specific language description;

encoding the graphical representation of the chemical structure into a vector comprising a plurality of numbers by determining a value for each feature of the graphical representation, wherein the plurality of numbers in the vector comprises a number for each feature of the graphical representation, and wherein the value for each feature comprises at least one of: one-hot encoding, word embeddings, or principal component analysis, wherein encoding the graphical representation further comprises:

receiving contextual metadata for the chemical structure;

encoding the contextual metadata into numerical form; and combining the contextual metadata with the graphical representation of the chemical structure into the vector, wherein the vector transforms the contextual metadata and the graphical representation of the chemical structure into a structured format, storing, by the computer system, the vector into a multi-modal searchable database;

accessing, by the computer system, the multi-modal searchable database based on the structured format for processing the vector by the machine learning model;

converting at least one of the multi-modal user query, the natural language query, or the built-in similarity search into a second graphical representation;

encoding the second graphical representation of the query into a second vector; and using the second vector to access the vector from the multi-modal database.

16. The computer program product of claim 15, wherein the operations further comprise:

receiving structural information for the chemical structure; and encoding the structural information into the vector; and wherein the contextual metadata comprises at least one of descriptive metadata, experimental metadata, structural metadata, or administrative metadata.

* * * * *